United States Patent [19]

Fujiki et al.

[11] Patent Number: 5,064,891
[45] Date of Patent: Nov. 12, 1991

[54] CURABLE SILICONE COMPOSITIONS

[75] Inventors: Hironao Fujiki, Takasaki; Mikio Shiono; Toshiaki Takahashi, both of Annaka, all of Japan

[73] Assignee: Shin-Etsu Chemical Co., Ltd., Tokyo, Japan

[21] Appl. No.: 525,047

[22] Filed: May 18, 1990

[30] Foreign Application Priority Data

May 19, 1989 [JP] Japan .................................. 1-126025
May 19, 1989 [JP] Japan .................................. 1-126026

[51] Int. Cl.$^5$ .............................................. C08K 5/54
[52] U.S. Cl. .................................. 524/264; 523/109; 524/266; 524/588; 524/731; 524/912
[58] Field of Search ............... 524/588, 912, 731, 266, 524/264; 525/478; 523/109

[56] References Cited

U.S. PATENT DOCUMENTS

| | | | |
|---|---|---|---|
| 4,248,750 | 2/1981 | Murakami et al. | 524/588 |
| 4,657,959 | 4/1987 | Bryan et al. | 524/731 |
| 4,752,633 | 6/1988 | Aasen et al. | 524/266 |
| 4,764,576 | 8/1988 | Ogawa et al. | 524/731 |
| 4,923,944 | 5/1990 | Yamada et al. | 524/588 |

FOREIGN PATENT DOCUMENTS 252706  11/1987  Japan .

*Primary Examiner*—Veronica P. Hoke
*Attorney, Agent, or Firm*—Oblon, Spivak, McClelland, Maier & Neustadt

[57] ABSTRACT

A curable silicone composition comprising:

(A) an organopolysiloxane having at least two silicon-bonded aliphatic unsaturated hydrocarbon radicals in its molecule;
(B) an organohydrogenpolysiloxane having at least three silicon-bonded hydrogen atoms in its molecule;
(C) a platinum family metal catalyst; and
(D) a nonionic surface active agent having a hydrophobic silicone portion and at least one hydrophilic polyol portion in its molecule. The curable silicone composition gives cured products having good hydrophilic properties and dimensional stability, and are especially suitable for use as a dental impression material.

4 Claims, No Drawings

CURABLE SILICONE COMPOSITIONS

BACKGROUND OF THE INVENTION

1. Field of the Invention

This invention relates to curable silicone compositions which give cured products especially excellent in hydrophilic properties.

2. Description of the Prior Art

Curable silicone compositions are excellent in the properties of cured products thereof, and are used widely for printing plates for lithography, mold release agents, adhesives, paints, sealants, reflecting sheets, dental impression materials, etc. As the impression material, particularly, addition-curing type curable silicone compositions are generally used. The addition-curing type curable silicone compositions have good curability, and are advantageous in that the compositions are cured with very little shrinkage and with no by-products. Furthermore, the cured products of the compositions of this type have excellent properties such as good dimensional stability, tastelessness and odorlessness, easy demoldability, etc.

Because the conventional curable silicone compositions are hydrophobic, however, it has been difficult to take an accurate impression of a wet surface by use of the compositions, because of the poor affinity of the compositions for the surface. For instance, when the conventional curable silicone composition is used as a dental impression material to take an impression of an inside part of a wet oral cavity, it is difficult to obtain a precise impression of detailed parts. In addition, when a model is formed by casting a plaster slurry in to the impression thus obtained, there arises a problem that the wettability of the impression with the plaster slurry is poor, making it difficult to obtain an accurate model.

In view of the above difficulties, curable silicone compositions improved in hydrophilicity by incorporating a nonionic surface active agent therein have been proposed [Lacy, A., Treleaven, S. & Tendresen, M., Cal. Dent. Assn. J., 5, 36–40 (1977); Norling, D. K. & Reisbicd, M. H., J. Pros. Dent., 42, 342–347 (1979)]. Also, U.S. Pat. Nos. 4,657,959 and 4,752,633 and Japanese Pre-examination Patent Publication (KOKAI) No. 252706/1987 propose curable silicone compositions in which a hydrophilicity-imparting agent comprising a silicone-modified polyether compound has been added.

The curable silicone composition comprising a nonionic surface active agent must contain a large amount of the nonionic surface active agent in order to improve satisfactorily the wettability of the cured composition by a plaster slurry. If the nonionic surface active agent is added in a large amount, however, the curing reaction of the composition is hindered, and the resultant cured product has poorer physical properties, such as an increased permanent set.

The curable silicone composition comprising a silicone-modified polyether compound, also, are inevitably accompanied by the problem of lowered physical properties of the cured products.

SUMMARY OF THE INVENTION

It is accordingly and object of this invention to provide curable silicone compositions which are good in curing properties thereof and the properties of cured products thereof, and are capable of yielding cured products with excellent hydrophilic properties.

The curable silicone composition of this invention comprises:

(A) an organopolysiloxane having at least two silicon-bonded aliphatic unsaturated hydrocarbon radicals in its molecule;

(B) an organohydrogenpolysiloxane having at least three silicon-bonded hydrogen atoms in its molecule;

(C) a platinum family metal catalyst; and (D) at least one member selected from the group consisting of:

(D-1) a nonionic surface active agent having a siloxane unit in its molecule, the siloxane unit having at least one silicon-bonded hydrogen atom or at least one silicon-bonded aliphatic unsaturated hydrocarbon radical, and (D-2) a nonionic surface active agent having a hydrophobic silicone portion and at least one hydrophilic polyol portion in its molecule.

The characteristic feature of the curable silicone compositions according to this invention resides in that the composition comprises the specified nonionic surface active agent (D-1) or (D-2) as component (D). With the nonionic surface active agent (D-1) or (D-2) incorporated, the cured products obtained from the curable silicone composition of this invention are excellent in physical properties such as dimensional stability, and exhibit good hydrophilicity (for instance, the contact angle between the surface of the cured product and water is not more than 65°).

The curable silicone composition of this invention, after cured, shows excellent hydrophilicity and are also excellent in physical properties such as dimensional stability. The compositions of this invention are therefore suitable applicable to a wide variety of uses, such as dental impression materials, printing plates for lithography, mold release agents, reflecting sheets, adhesives, sealants, contact lenses, silicone implants, bandages for wounds, etc. Especially, the compositions of this invention are the most suitable for use as a dental impression material.

DETAILED DESCRIPTION OF THE INVENTION

Component (A)

The organopolysiloxane used as component (A) of the composition of this invention has at least two silicon-bonded aliphatic unsaturated hydrocarbon radicals in one molecule thereof, and may have straight-chain or branched form of have a two- or three-dimensional network structure or a mixture thereof. The aliphatic unsaturated hydrocarbon radicals include, for example, $C_1$–$C_6$ alkenyl groups such as vinyl, allyl, butenyl, pentenyl, and hexenyl of which the vinyl radical is preferred. Silicone-bonded organic radicals other than the aliphatic unsaturated hydrocarbon radicals include, for example, $C_1$–$C_{10}$ saturated monovalent hydrocarbon radicals, e.g., $C_1$–$C_8$ alkyl radicals such as methyl, ethyl, and propyl; $C_6$–$C_{10}$ aromatic hydrocarbon radicals such as phenyl and tolyl; $C_5$–$C_{10}$ alicyclic hydrocarbon radicals such as cyclohexyl and cycloheptyl; and radicals corresponding to the above hydrocarbon radicals in which part or all of the carbon-bonded hydrogen atoms are substituted by halogen atoms or the like, such as chloromethy, and 3,3,3-trifluoropropyl. Of these organic radicals, preferred are methyl, phenyl and 3,3,3-trifluoropropyl. Particularly preferable examples of the organopolysiloxane of component (A) include those in which all of the substituents other than the aliphatic unsaturated hydrocarbon radicals are the methyl radicals, or admixture of methyl and phenyl radicals.

The viscosity of the organopolysiloxane of component (A) at 25° C. is generally 50 cSt or above, preferably from 100 to 5,000,000 cSt.

The organopolysiloxane of component (A) differs from the nonionic surface active agent (D-1) or (D-2), described below, in that the organopolysiloxane has no alkylenoxy radical or polyol radical (i.e., organic radical having a plurality of hydroxyl radicals derived from a polyhydric alcohol) in the molecule thereof.

Component (B)

The organohydrogenpolysiloxane of component (B) of the composition according to this invention has at least three silicon-bonded hydrogen atoms in its molecule, and may have any of straight-chain, branched, cyclic and network structures, of which the straight-chain structure is preferred.

In the composition of this invention, addition reaction is performed between the silicon-bonded hydrogen atom in the (B) organohydrogenpolysiloxane and the aliphatic unsaturated hydrocarbon radical in the organopolysiloxane (A) mentioned above, whereby a cured product is formed.

In the organohydrogenpolysiloxane, silicon-bonded organic radicals other than the silicon-bonded hydrogen atoms include, for example, $C_1$-$C_{10}$ saturated monovalent hydrocarbon radicals as exemplified above as one of substituents in the organopolysiloxane of component (A).

The viscosity of the organohydrogenpolysiloxane of component (B) at 25° C. is generally from 0.5 to 10,000 cSt, preferable from 1 to 1,000 cSt. Where component (E), described later, is incorporated in the composition, it is preferable that the viscosity of the organohydrogenpolysiloxane (B) is in the range from 2 to 1,000 cSt, particularly from 5 to 150 cSt.

The amount of component (B) blended in the composition of this invention is generally so selected that the number of the silicon-bonded hydrogen atoms in component (B) per one aliphatic unsaturated hydrocarbon radical in component (A) is preferably from 0.5 to 10, more preferably from 0.75 to 5. If the amount of component (B) blended is too large, the cured product of the composition obtained would be brittle or an excess of hydrosilyl radicals (Si-H) might be left in the cured product, causing changes in propertied with time. If the amount is too small, on the other hand, unsatisfactory cure of the composition would be liable to result.

The organohydrogenpolysiloxane used as component (B) is distinct from the nonionic surface active agent (D-1) or (D-2), described below, in that the organohydrogenpolysiloxane (B) has no alkylenoxy radical or polyol radical.

Component (C)

The platinum family metal catalyst as component (C) of the composition of this invention may be selected, without any limitation, from those which are conventionally used for addition-curing type curable silicone compositions, for instance, platinum black, platinum supported on silica, carbon black or the like, chloroplatinic acid, alcohol-modified chloroplatinic acids, platinum-vinylsiloxane complexes, chloroplatinic acid-olefin complexes, etc. Alcohol-modified chloroplatinic acids, platinum-vinylsiloxane complexes and chloroplatinic acid-olefin complexes are particularly preferred, from the viewpoint of storage stability and reactivity of the composition obtained, etc.

The amount of component (C) blended is appropriately adjusted so as to obtain a desired curing rate. In general, the amount of component (C) in terms if platinum quantity is from 0.1 to 500 ppm, preferably from 1 to 300 ppm, based on component (A). If the amount of component (C) is too small, unsatisfactory cure is liable to result.

Component (D)

In the curable silicone composition of this invention, the nonionic surface active agent (D-1) and/or (D-2) is incorporated as component (D).

Nonionic Surface Active Agent (D-1)

This nonionic surface active agent has a siloxane unit and at least one, preferable from 3 to 150, hydrogen atoms or aliphatic unsaturated hydrocarbon radicals in the form of being bonded to a silicon atom of the siloxane unit, in its molecule.

The nonionic surface active agent (D-1), by virtue of the hydrogen atoms of aliphatic unsaturated hydrocarbon radicals contained therein as above-mentioned, is believed to be incorporated effectively into the cured product formed by the addition curing reaction between component (A) and component (B). Therefore, the cured product obtained from the composition of this invention retains the hydrophilic property for a long time, is excellent in physical properties such as dimensional stability, and is effectively free from the problems such as bleeding of the nonionic surface active agent to the surface of the cured product. If a nonionic surface active agent containing no hydrogen atoms or aliphatic unsaturated hydrocarbon radicals is used, the cured product of the composition obtained is poor in physical properties such as dimensional stability, and loses the hydrophilic property in a short time.

The nonionic surface active agent (D-1) preferably has at least one, more preferably from 1 to 15, alkylenoxy radicals in its molecule. The alkylenoxy radicals include, for example, methylenoxy, ethylenoxy, propylenoxy, hydroxylalkyl-substituted ethylenoxy, and the like, of which the ethylenoxy radical being preferred.

One specific example of the nonionic surface active agent of component (D-1) is a nonionic surface active agent represented by the following formula [I]:

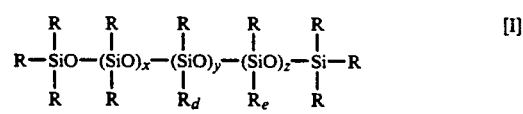

wherein a plurality of R may be the same or different and each are a $C_1$ to $C_8$ univalent hydrocarbon radical, for instance, an alkyl radical such as methyl, ethyl, propyl, and butyl; a cycloalkyl radical such as cyclohexyl, and cycloheptyl; an aromatic hydrocarbon radical such as phenyl, tolyl, and xylyl; or radicals corresponding to the above radicals in which part or all of the carbon-bonded hydrogen atoms have been substituted by halogen atoms such as fluorine, chlorine, etc., for instance, chloromethyl, 3,3,3-trifluoropropyl, etc. Among these preferred in the methyl radical. $R_d$ is a hydrogen atom or aliphatic unsaturated hydrocarbon radical, for instance, viny, allyl, bùtenyl, hexenyl, or the like, preferably vinyl. Re is a radical represented by the formula [II]:

$$-R^1O-(C_2H_4O)_a-R^2 \quad [II]$$

wherein $R^1$ is a $C_1$ to $C_6$ bivalent hydrocarbon radical, for instance, methylene, ethylene, propylene, tetramethylene, pentamethylene, hexamethylene, or the like, preferably propylene; $R^2$ is a hydrogen atom or $C_1$ to $C_6$ univalent hydrocarbon radical, for instance, methyl, ethyl, propyl, butyl, and the like, preferably methyl; a is an integer of one or more, and is preferably an integer of from 3 to 20 because the cured product of the composition obtained can acquire a sufficiently small contact angle with water. The symbol x is an integer of 0 or more, preferably 0. The symbol y is an integer of 1 or more, preferably from 3 to 150, and more preferably from 3 to 10. The symbol z is an integer of 1 ore more, preferably from 1 to 15, and more preferably from 2 to 10.

Another specific example of the nonionic surface active agent of component (D-1) is represented by the following formula [III]:

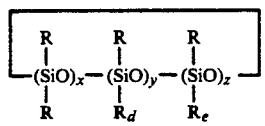

wherein R, $R_d$, $R_e$, x, y and z are as defined above.

In the formula [III], R is preferably the methyl radical, and Re is preferably a radical represented by the following formula [IIa]:

$$-R^1O-(C_2H_4O)_a-CH_3 \quad [IIa]$$

where $R^1$ is as defined above, and a is an integer of from 3 to 20. Furthermore, x, y and z are preferably such integers that the value of $x+y+z$ is from 3 to 10, particularly 4.

The nonionic surface active agents (D-1) described above may be used either singly or in combination of two or more.

The amount of the nonionic surface active agent (D-1) to be blended in the composition is generally from 0.5 to 15 parts by weight per 100 parts by weight of component (A), and is desirably controlled appropriately according to the amounts of component (A) and component (B) so that the molar ratio of the silicon-bonded hydrogen atoms to the silicon-bonded aliphatic unsaturated hydrocarbon radicals in the composition may be in the range of from 0.5 to 10, preferably from 0.75 to 5.

Nonionic Surface Active Agent (D-2);

In the curable silicone composition of this invention, the nonionic surface active agent (D-2) may be used as component (D), either in place of or in combination with the nonionic surface active agent (D-1).

The nonionic surface active agent (D-2) has a hydrophobic silicone portion and at least one, preferably two or more, hydrophilic polyol potions in its molecule.

Illustrative examples of the hydrophobic silicone potion in the nonionic surface active agent (D-2) include polyorganosiloxane chains such as a dimethylsiloxane chain, a diphenylsiloxane chain, a methylphenylsiloxane chain, etc. On the other hand, examples of the hydrophilic polyol potions include polyol radicals (univalent organic radicals having a plurality of hydroxyl radicals derived from polyhydric alcohols), etc. It is preferred that the hydrophilic polyol portions do not contain ethylenoxy radicals. A preferable value of the molar ratio of the hydrophobic silicone portion to the hydrophilic polyol portions, for instance, the molar ratio of the organosiloxane unit to the polyol radicals is generally in the range of from 1 to 10.

Specific examples of the nonionic surface active agent (D-2) include surface active agents represented by the following general composition formula [IV]:

wherein p is a number in the rage of $0.05 \leq p \leq 2.5$, and q is a number in the range of $0.1 \leq q \leq 0.35$, provided p+q is a number of $1 \leq p+q \leq 2.8$; $R^3$ is a hydrogen atom or $C_1$ to $C_8$ univalent hydrocarbon radical, e.g., alkyl radials such as methyl, ethyl, propyl, butyl, and the like, aromatic hydrocarbon radicals such as phenyl, tolyl, and like, substituted hydrocarbon radicals corresponding to these radical in which part or all of the carbon-bonded hydrogen atoms have been substituted by fluorine, chlorine or other halogen atoms or the like, such as 3,3,3-trifluoropropyl, and chloromethyl, aliphatic unsaturated hydrocarbon radicals such as vinyl and allyl; and $R^4$ is a polyol radical represented by the following formula [V]:

$$-R^5OCH_2C(CH_2OH)_mR^6_n \quad [V]$$

where $R^5$ is a $C_1$-$C_6$ bivalent hydrocarbon radical, for instance, an alkylene radical such as methylene, propylene, tetramethylene, pentamethylene, and the like, preferably propylene; $R^6$ is a $C_1$-$C_6$ univalent hydrocarbon radical, for example, methyl, ethyl, propyl or the like, preferably ethyl; and m is an integer of 2 or 3, and n is an integer of 0 or 1, provided m+n=3.

A preferred, more specified example of the nonionic surface active agent (D-2) is represented by the following formula [VI]:

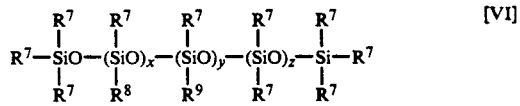

wherein a plurality of $R^7$ may be the same or different and each a $C_1$ to $C_8$ univalent hydrocarbon radical, preferably a saturated one of the hydrocarbon radicals described as examples of $R^3$ in the formula [IV] above, more preferably the methyl group; $R^8$ is a hydrogen atom or aliphatic unsaturated one of the hydrocarbon radicals described as examples of $R^3$ in the formula [IV] above, preferably hydrogen or vinyl; $R^9$ is the same as $R^4$ represented by the formula [V] above; x is an integer in the range of $x \geq 0$, preferably an integer of from 0 to 10; y is an integer in the range of $y \geq 1$, preferably an integer of from 1 to 10; and z is an integer of in the range of $z \geq 0$, preferably an integer of from 0 to 10. It is further preferable that x=0, y is an integer of from 1 to 5, and z is an integer of from 0 to 5. It is particularly preferable that x=0, y is an integer of from 1 to 5, and z is 0 to 1.

The nonionic surface active agent (D-2) represented by the formula [VI] can be produced by methods known in the art. For instance, an organohydrogenpolysiloxane having at least one silicon-bonded hydrogen atom in its molecule may be reacted with a polyhydric alcohol having an alkenyl radical at an end of its molecule, in the presence of a platinum catalyst. After the reaction is over, unreacted reactants are distilled off, and the residue is treated with activated carbon give a reaction mixture, which is generally a mixture of a plurality of silicone compounds represented by the formula [VI]. The mixture may be directly used as component (D), or, alternatively, the mixture may be separated into the respective compounds by distillation or the like and one of the compounds may be used singly.

Generally, the amount of the nonionic surface active agent (D-2) blended in the composition is preferably from 0.1 to 20 parts by weight, more preferably from 0.2 to 15 parts by weight, and most preferably from 0.5 to 5 parts by weight, per 100 parts by weight of component (A). With such an amount of the nonionic surface active agent (D-2) blended in the composition of this invention, a cured product of the composition is effectively obtainable which has appropriate hydrophilicity and is excellent in physical properties such as dimensional stability.

Where the nonionic surface active agent (D-2) has a silicon-bonded hydrogen atom or a silicon-bonded aliphatic unsaturated hydrocarbon radical, it is desirably to control the molar ratio of the silicon-bonded hydrogen atoms to the silicon-bonded aliphatic unsaturated hydrocarbon radicals in the composition (hydrogen atoms/aliphatic unsaturated hydrocarbon radicals) to within the rage of from 0.5 to 10, preferably from 0.75 to

Other Components

In the curable silicone composition of this invention, if required, compounding additives which are known per se, for instance, fillers, dyes, pigments, reinforcing agents, metallic powder, perfumes, fluidity-controlling agents, plasticizers, reaction retarders, etc., can be blended insofar as the compounding additives do not impair the hydrophilicity and the physical properties such as dimensional stability of the cured products obtained from the composition. For instance, reinforcing fillers usable in the compositions include fumed silica, precipitated silica, powdered quartz, powder of fused quartz, diatomaceous earth, calcium carbonate, etc. Dyes or pigments usable in the composition include inorganic pigments such as titanium oxide, cobalt aluminate, titanium yellow, red iron oxide, carbon black, etc., and organic dyes and pigments.

Curable Silicone Composition

Generally, the curable silicone composition of this invention is prepared as a two-pack type composition comprising a part which contains component (A) and another part which contains component (B), and the two parts are mixed with each other to effect curing at the time of use.

Where the nonionic surface active agent (D-1) of component (D) contains a silicon-bonded hydrogen atom, the surface active agent is blended in the part containing the component (B); while, on the other hand, where containing a silicon-bonded aliphatic unsaturated hydrocarbon radical, the surface active agent is blended in the part containing the component (A). In the case where the nonionic surface active agent (D-2) is used as component (D) and contains a silicon-bonded hydrogen atom or silicon-bonded aliphatic unsaturated hydrocarbon radical, the surface active agent is blended in either the part containing the component (A) or the part containing the component (B) depending on the reactive according to the radical contained, in the same manner described above in respect of the surface active agent (D-1). In the case where the surface active agent (D-1) dose not contain a silicon-bonded hydrogen atom or aliphatic unsaturated hydrocarbon radical, the surface active agent may be blended in either of the part containing the component (A) and the part containing the component (B). The other components may be blended in either of the part containing the component (A) and the part containing the component (B).

Besides, the curable silicone composition of this invention may also be prepared as a one-pack type composition which contains all the above-mentioned components. In that case, it is desirable to blend in the composition a reaction retarder which is known per se. The reaction retarder usable includes, for example, acetylene alcohols, siloxane-modified acetylene alcohols, high-vinyl-content organopolysiloxanes such as tetravinyltetramethylcyclotetrasiloxane, triallyl isocyanurate, and so on.

The curable silicone composition of this invention is capable of being cured in a short time (for instance, in a few minutes), at room temperature or by heating, if required. The composition of this invention retains good hydrophilicity during and after curing, and shows good wettability in contact with hydrophilic materials or water-containing materials. Besides, the cured products obtained from the composition of this invention are excellent in properties such as dimensional stability, and are free of bleeding of the nonionic surface active agent to the surface thereof. Accordingly, the compositions of this invention, when used in a moist atmosphere such as the inside of an oral cavity, are capable of forming an accurate impression, and are therefore especially suitable for use as a dental impression material. Moreover, the compositions of this invention are applicable to uses where hydrophilicity is required, such as a modeling material, and other wide range of uses.

EXAMPLES

This invention will now be described in detail referring to Examples and Comparative Examples below. In the following examples, "parts" and "%" represent "parts by weight" and "% by weight", respectively.

Examples 1 and 2, Comparative Example 1

In these examples, a total of three compositions were prepared each of which comprised 100 parts of a dimethylvinylsiloxy-endblocked methylvinylpolysiloxane having a backbone chain composed of dimethylsiloxane units, endblocked with a dimethylvinylsiloxy group at both ends and having a viscosity of 5,000 cSt at 25° C., 2 parts of a methylhydrogenpolysiloxane represented by the average composition formula:

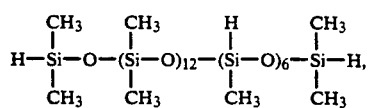

a 1% isopropyl alcohol solution of chloroplatinic acid in such an amount that the amount of platinum was 40 ppm based on the amount of the methylvinylpolysiloxane, and 1 part of a surface active agent shown in Table 1, except that the composition of Comparative Example 1 did not contain a surface active agent.

Each of the compositions thus obtained was applied to a smooth glass plate, and cured at room temperature for 10 minutes. One drop of distilled water was placed carefully on the surface of the cured product. After 3 minutes, the contact angle between the water drop and surface of the cured product (hereinafter referred to simply as "water contact angle") was measured. The results are shown in Table 1.

TABLE 1

|  | Surface active agent | Water contact angle (°) |
|---|---|---|
| Examples 1 | Polyalkylene oxide-modified polymethylhydrogensiloxane*1 | 65 |
| 2 | Polyalkylene oxide-modified polymethylhydrogensiloxane*2 | 61 |
| Comparative Example 1 |  | 93 |

*1This surface active agent is represented by the following formula:

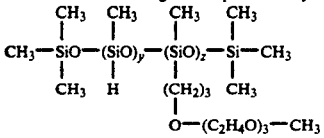

where y has an average value of 5.5, and z has an average value of 2.5.
*2This surface active agent is represented by the following formula:

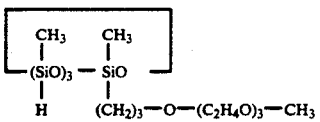

Each of the three compositions obtained respectively in Examples 1 and 2 and Comparative Example 1 was cast into a 2 mm deep split mold comprising an upper mold and lower mold both measuring 20 mm×20 mm×1 mm (depth), and was cured. After the composition was cured, the upper half of the mold was removed, then the upper half of the cured product was cut off, and the water contact angle of the cut surface of the cured product was measured in the same manner as in Example 1. The water contact angles of the cut surfaces of the cured products obtained in Examples 1 and 2 and Comparative Example 1 were 63°, 60° and 94°, respectively.

COMPARATIVE EXAMPLES 2 TO 4

In each of these examples, a composition was prepared in the same manner as in Example 1 except that a surface active agent shown in Table 2 was used. For each composition thus obtained, the water contact angle was measured in the same manner as in Example 1. The results are shown in Table 2.

TABLE 2

|  | Surface active agent | Water contact angle (°) |
|---|---|---|
| Comparative Examples |  |  |
| 2 | Polyalkylene oxide-modified polymethylsiloxane*1 | <10 |
| 3 | Polyalkylene oxide-modified polymethylsiloxane*2 | 79 |
| 4 | Alkyl-endblocked polyalkylene oxide*3 | 91 |

*1A product by Shin-Etsu Chemical Co., Ltd., KF-618
*2A product by Shin-Etsu Chemical Co., Ltd., KF-351A
*3A product by Nissan Chemical Ind., Ltd., Uniox ® M200.

Either of the surface active agents used in Comparative Examples 2 and 3 does not contain a silicon-bonded hydrogen atom or aliphatic unsaturated hydrocarbon radical, and does not have a polyol radical. The composition of Comparative Example 2, when visually checked 24 hours after the cure, showed the surface active agent bleeding out to the surface of the cured product. The composition of Comparative Example 3, when visually examined 48 hours after the cure, showed the bleeding of the surface active agent to the surface of the cured product.

The surface active agent used in Comparative Example 4 does not contain a siloxane unit. This composition had a slow curing rate, and showed the bleeding of the surface active agent to the surface of the cured product immediately upon the cure. On the other hand, the cured products obtained in Examples 1 and 2 did not show bleeding of the surface active agent even after left to stand at room temperature for 10 days.

EXAMPLES 4 AND 4, COMPARATIVE EXAMPLES 5 TO 8

In each example, each of the cured products obtained in Examples 1 and 2 and Comparative Examples 1 to 4 was cut into two pieces, one of which was left to stand at room temperature for 10 days, whereas the other piece was washed with flowing water for 2 days, to obtain two kinds of test pieces. For the two kinds of test pieces thus obtained, the water contact angle was measured in the same manner as in Example 1. The results are shown in Table 3.

Examples 3 and 4 were carried out by use of the cured products obtained in Examples 1 and 2, respectively, whereas Comparative Examples 5 to 8 were carried out by use of the cured products obtained in Comparative Examples 1 to 4, respectively.

TABLE 3

|  | Water contact angle (°) | |
|---|---|---|
|  | After left to stand for 10 days | After washed in flowing water for 2 days |
| Examples |  |  |
| 3 | 63 | 62 |
| 4 | 60 | 60 |
| Comparative Examples |  |  |
| 5 | 91 | 92 |
| 6 | 28 | 39 |
| 7 | 82 | 85 |
| 8 | 93 | 95 |

EXAMPLES 5 AND 6, COMPARATIVE EXAMPLES 9 TO 11

The compositions obtained in Examples 1 and 2 and Comparative Examples 2, 3 and 4 were each cast into a mold to form molded products in the shape of rectangular parallelopiped, measuring 50 mm×20 mm×4 mm, with two marks provided on a surface of the product at an interval of 40 mm along the longitudinal direction of the product. The molded products thus obtained were divided into two groups. One group of the molded products were left to stand at room temperature and a relative humidity of 20%, whereas the other group of the molded products were washed with flowing water for 24 hours. After these treatments, the spacing between the two scale marks on each of the molded products was measured, and rate of dimensional charge was calculated from the formula: [40-(spacing between scale marks after treatment)]/40. The results are shown in Table 4.

TABLE 4

| | Rate of dimensional change | |
|---|---|---|
| | After left to stand at room temperature and 20% RH | After washed in flowing water for 24 hr |
| Examples | | |
| 5 | +0.04 | +0.09 |
| 6 | +0.02 | +0.08 |
| Comparative Examples | | |
| 9 | +0.05 | −0.74 |
| 10 | +0.02 | −0.65 |
| 11 | −0.08 | −0.79 |

EXAMPLE 7, COMPARATIVE EXAMPLES 12 AND 13

Pasty materials $A_1$ to $A_3$ were prepared by mixing the following ingredients according to the formulations shown in Table 5, and agitating the mixtures.

A dimethylpolysiloxane oil endblocked with a dimethylvinylsiloxy radical at both ends and having a viscosity of 100 cSt (25° C.).

A dimethylpolysiloxane gum endblocked with a dimethylvinylsiloxy radical at both ends (vinyl content: 0.0025 mol %) and having a relative viscosity in xylene solution of 2.8.

An octyl alcohol solution of chloroplatinic acid (platinum content: 1 wt. %).

Powdered quartz 4 μm in average particle diameter. Liquid paraffin.

Diatomaceous earth 2 μm in average particle diameter.

Also, pasty materials $B_1$ to $B_3$ were prepared by admixing the above ingredients with the following ingredients according to the formulations shown in Table 5, and agitating the admixtures.

A methylhydrogenpolysiloxane endblocked with a dimethylhydrogensiloxy radical at both ends (methylhydrogensiloxane unit content: 33 mol %) and having a viscosity of 12 cSt (25° C.).

A surface active agent represented by the following formula (i) or (ii):

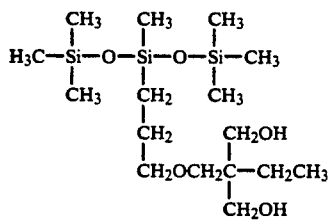

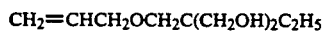

The pasty material $B_1$ contains the surface active agent (i), whereas the pasty material $B_2$ does not contain a surface active agent, and the pasty material $B_3$ contains the surface active agent (ii).

By rapid mixing of 1 g of each of the pasty materials $A_1$, $A_2$ and $A_3$ with 1 g of each of the pasty materials $B_1$, $B_2$ and $B_3$, respectively, three compositions were prepared. Each of the compositions thus obtained was cast into a cylindrical mold, 19 mm in diameter by 1 mm in thickness, placed on a glass plate. After removing excess portion of the composition by a spatula, the mold was covered with another glass plate, and the composition in the mold was cured at room temperature for 10 minutes. Then, a drop of distilled water was placed carefully on the surface of each of the cured products thus obtained, and the contact angle between the water drop and the surface of each cured product was measured by a goniometer, after 30 seconds and after 3 minutes. The results are shown in Table 5.

TABLE 5

| | Example 7 | | Comparative Example 12 | | Comparative Example 13 | |
|---|---|---|---|---|---|---|
| | $A_1$ | $B_1$ | $A_2$ | $B_2$ | $A_3$ | $B_3$ |
| Dimethylpolysiloxane oil (parts) | 80 | 75 | 80 | 75 | 80 | 75 |
| Dimethylpolysiloxane gum (parts) | 20 | 20 | 20 | 20 | 20 | 20 |
| Methylhydrogenpolysiloxane (parts) | 0 | 5 | 0 | 5 | 0 | 5 |
| Octyl alcohol solution of chloroplatinic acid (parts) | 0.8 | 0 | 0.8 | 0 | 0.8 | 0 |
| Powdered quartz (parts) | 190 | 190 | 190 | 190 | 190 | 190 |
| Diatomaceous earth (parts) | 20 | 20 | 20 | 20 | 20 | 20 |
| Liquid paraffin (parts) | 20 | 20 | 20 | 20 | 20 | 20 |
| Surface active agent | | | | | | |
| Kind | — | (i) | — | — | — | (ii) |
| Amount (parts) | — | 4 | — | — | — | 4 |
| Water contact angle (°) | | | | | | |
| After 30 sec. | 65 | | 100 | | 91 | |
| After 3 min. | 61 | | 99 | | 82 | |

We claim:
1. A curable silicone composition comprising:
(A) an organopolysiloxane having at least two silicon-bonded aliphatic unsaturated hydrocarbon radicals in its molecule;
(B) an organohydrogenpolysiloxane having at least three silicon-bonded hydrogen atoms in its molecule;
(C) a platinum family metal catalyst; and
(D) a nonionic surface active agent having a hydrophobic silicone portion and at least one hydrophilic polyol portion in its molecule, wherein the nonionic surface active agent is represented by the following general composition formula [IV]:

$$(R^3)_p(R^4)_q SiO_{\frac{4-p-q}{2}} \qquad [IV]$$

wherein
p is a number in the range of $0.05 \leq p \leq 2.5$, and
q is a number in the range of $0.1 \leq q \leq 0.35$, provided p+q is in the range of $1 \leq p+q \leq 2.8$;
$R^3$ is a hydrogen atom or $C_1$ to $C_8$ univalent hydrocarbon radical, and $R^4$ is a polyol radical represented by the following formula [V]:

$$-R^5OCH_2C(CH_2OH)_mR^6_n \quad [V]$$

wherein $R^5$ is a $C_1$ to $C_6$ bivalent hydrocarbon radical, $R_6$ is a $C_1$ to $C_6$ univalent hydrocarbon radical, m is an integer of 2 or 3, and n is an integer of 0 or 1, provided m+n=3.

2. The composition according to claim 1, wherein the nonionic surface active agent is represented by the following formula [VI]:

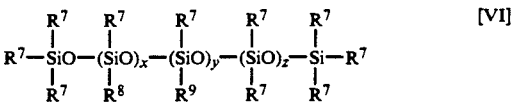

wherein
 x and z are each an integer of 0 or more,
 y is an integer of 1 or more,
 $R^7$ may be the same or different, and are each a $C_1$ to $C_8$ univalent hydrocarbon radical,
 $R^8$ is a hydrogen atom or aliphatic unsaturated hydrocarbon radical, and
 $R^9$ has the same meaning as $R^4$.

3. The composition according to claim 1, wherein the nonionic surface active agent is blended in an amount of from 0.1 to 20 parts by weight per 100 parts by weight of component (A).

4. A cured product obtained by curing the curable silicone composition as claimed in claim 1.

* * * * *